United States Patent [19]
Adams

[11] Patent Number: 5,383,915
[45] Date of Patent: Jan. 24, 1995

[54] WIRELESS PROGRAMMER/REPEATER SYSTEM FOR AN IMPLANTED MEDICAL DEVICE

[75] Inventor: Theodore P. Adams, Edina, Minn.

[73] Assignee: Angeion Corporation, Plymouth, Minn.

[21] Appl. No.: 13,028

[22] Filed: Jan. 28, 1993

Related U.S. Application Data

[63] Continuation of Ser. No. 682,966, Apr. 10, 1991, abandoned.

[51] Int. Cl.6 .............................................. H04B 7/00
[52] U.S. Cl. .................................... 607/60; 607/32; 607/30; 128/903
[58] Field of Search .......................... 607/30, 32, 60; 128/903, 904, 706, 710

[56] References Cited

U.S. PATENT DOCUMENTS

| | | | |
|---|---|---|---|
| 3,253,588 | 5/1966 | Vuilleumier et al. | 128/903 |
| 3,986,498 | 10/1976 | Lewis | 128/706 |
| 4,361,153 | 11/1982 | Slocum et al. | 128/903 |
| 4,522,213 | 6/1985 | Wallroth et al. | 128/903 |
| 4,561,443 | 12/1985 | Hogrefe et al. | 128/903 |
| 4,706,689 | 11/1987 | Man | 128/903 |
| 4,854,328 | 8/1989 | Pollack | 128/903 |
| 4,886,064 | 12/1989 | Strandberg | 128/903 |
| 4,944,299 | 7/1990 | Silvian | |
| 4,952,928 | 8/1990 | Carroll et al. | 128/903 |
| 4,958,632 | 9/1990 | Duggan | |
| 4,958,645 | 9/1990 | Cadell et al. | 128/903 |
| 5,012,806 | 5/1991 | De Bellis | 128/903 |
| 5,153,584 | 10/1992 | Engira | 128/903 |

*Primary Examiner*—Angela D. Sykes
*Assistant Examiner*—Kennedy J. Schaetzle
*Attorney, Agent, or Firm*—Patterson & Keough

[57] ABSTRACT

A sterilizable programmer repeater system for retransmission of a programmed code via an RF data link from a pacemaker or defibrillator programmer to an implanted pacemaker or defibrillator which can be used in the operating theater. Coded program information from a remotely placed programmer is data linked by an RF transmitter to a programmer repeater placed externally adjacent to an implanted pacemaker or defibrillator. The received coded program data information is rebroadcast by a transmitter in the programmer repeater to the implanted pacemaker or defibrillator. Coded program data information from the implanted pacemaker or defibrillator is also sent in the reverse direction from the implanted device to the remotely linked placed programmer.

16 Claims, 2 Drawing Sheets

WIRELESS PROGRAMMER/REPEATER SYSTEM FOR AN IMPLANTED MEDICAL DEVICE

CROSS REFERENCES TO CO-PENDING APPLICATIONS

This is a continuation of application Ser. No. 07/682,966 filed Apr. 10, 1991 now abandoned.

BACKGROUND OF THE INVENTION

1. Field of the Invention

The present invention pertains to pacemakers or defibrillators, and more particularly, pertains to remote programming of a pacemaker or defibrillator by the use of a radio frequency repeater device placed in close proximity to the implanted stimulation device.

2. Description of the Prior Art

Prior art implanted devices, such as pacemakers or defibrillators, are normally packaged in titanium cases. The metallic case provides hermiticity and serves as a shield for stray electrical fields which may interfere with operation of the device's electronics. The shield also has the effect of attenuating the RF signals from a programming device, which are necessary to configure the electronics for a given patient. Because of the shielding effects of the metal case, and of the patient's own body, it is usually necessary to place the programing antenna as close to the implanted device as the exterior of the patient's body permits.

The programming device is usually a large nonsterilizable box with an antenna connected to it with a coiled umbilical cord. In surgery, the antenna wand is usually covered with a long sterile plastic bag. The physician then handles the wand in the sterile field. The limited space usually requires the physician to hold the wand and give verbal instructions to a nurse who is operating the programmer at a spaced distance. The springiness of the coiled cord make setting the wand down risky, and the distance from the physician to the programmer usually precludes his seeing the programmer display. The whole situation is unwieldy. Sometimes the coiled cord caused the wand to repel and even fall on the floor of the operating room, requiring. recovering the wand with a new sterile plastic bag.

The present invention overcomes the deficiencies of the prior art by providing a small sterilizable battery-operated repeater unencumbered by connecting cords or wires which repeats informational data code to the pacemaker or defibrillator via RF transmissions from a remotely placed programmer.

Shortcomings of the prior art methods can be summarized by noting that they place incompatible, essentially contradictory requirements on both apparatus and human participants in the programming procedure. The element that transmits and receives RF signals to and from the implanted stimulator must be sterilizable. While it is outside the patient's body, it is well within the sterile zone or field that must be maintained in and near the patient in an operating room. Further requirements are that it must be accurately positionable and easily maintained in that position. For effective use it should also be comparatively small.

The programming unit, on the other hand, is inherently nonsterilizable, because it incorporates electromechanical input components (pushbuttons, switches, dials) and electromechanical and electronic readout devices (gauges, meters, digital displays), and these do not lend themselves to sterilizable design. Furthermore, the programming unit can be more easily and accurately used if it is permitted to grow to a comfortably large size, affording room for finger-sized pushbuttons and easily read displays. These incompatibilities are bridged in the prior art by means of an interconnecting cable, coiled for flexibility, but still heavy enough and stiff enough to disturb the position of the antenna element.

The contradictory human requirements arise because the attending surgeon must address two functions simultaneously: There is the mechanical task of maintaining the antenna component in the right position in the presence of the forces on it exerted by the cable, and the intellectual task of articulating instructions to an assistant, this without benefit of visual feedback from observing the displays as his or her instructions are executed by the assistant, or the motor feedback that would be derived if he or she were personally executing the programming. It will be seen that the present invention eliminates self-contradictory requirements from both the human participant and the apparatus.

SUMMARY OF THE INVENTION

The general purpose of the present invention includes a small battery-operated repeater which can be sterilized and placed on the patient over the implanted device. The repeater has a sensitive RF receiver tuned to the transmission frequency of the programmer's transmitter and a transmitter, and antenna which aligns near the implanted device's antenna which simply retransmits the code from the programmer to the implanted device. Because the repeater case is non-metallic, and since its receiver antenna can be made large relative to the implanted device's antenna, it can receive signals from the programmer at a much greater distance. The device works the same way in reverse when the implanted device is transmitting data out. This circumvents the problem of invading the sterile field with a cumbersome programming wand and allows the programmer to be placed at a greater distance from the patient in a crowded operating room. In addition, the physician could stand near the programmer to observe the display.

In a second embodiment, programmed data from the programmer is data-linked by an alternative transmission frequency for a different medium, i.e., infrared or ultrasound. The repeater then acts in a similar fashion, and converts the coded signal it receives from the transmitter/receiver to that to which the implanted device can receive and interpret. In this embodiment, greater transmission distances may be achieved by choice of the initial transmission frequency medium.

According to one embodiment of the present invention, there is provided a small sterilizable battery-operated repeater for two-way communication between a programmer unit and an implanted stimulation device. Program information from a programmer is transmitted from an antenna in the form of coded radio frequency from a location adequately spaced from the operating table to a receiving antenna in the repeater which is placed on the patient in close proximity to the implanted device. Information is received and rebroadcast by a transmitter and another antenna in the repeater to an antenna on the subcutaneously located stimulation device.

One significant aspect and feature of the present invention is a sterilizable battery-operated telemetry repeater system for a pacemaker or a defibrillator.

Another significant aspect and feature of the present invention is a remote site programmer for a repeater.

A further significant aspect and feature of the present invention is a repeater which is a data link between a programmer and an implanted device.

An additional significant aspect and feature of the present invention is the replacement of connecting cords or cables by an RF data link through a repeater.

A further feature is that the small and sterile free-standing telemetry repeater can in many cases be held and maintained in the desired positions on the chest of the supine patient by gravity alone.

Another feature is that a clear path from programming unit to telemetry repeater could be maintained by the simplest of measures, such as a pair of strings serving as reminders that the beam (RF, IR or ultrasound) not be inadvertently obstructed.

Having thus described one embodiment of the present invention, it is the principal object hereof to provide a repeater system for linking data to and from a programmer and an implanted device with a small battery-operated repeater for placement on a patient's chest.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
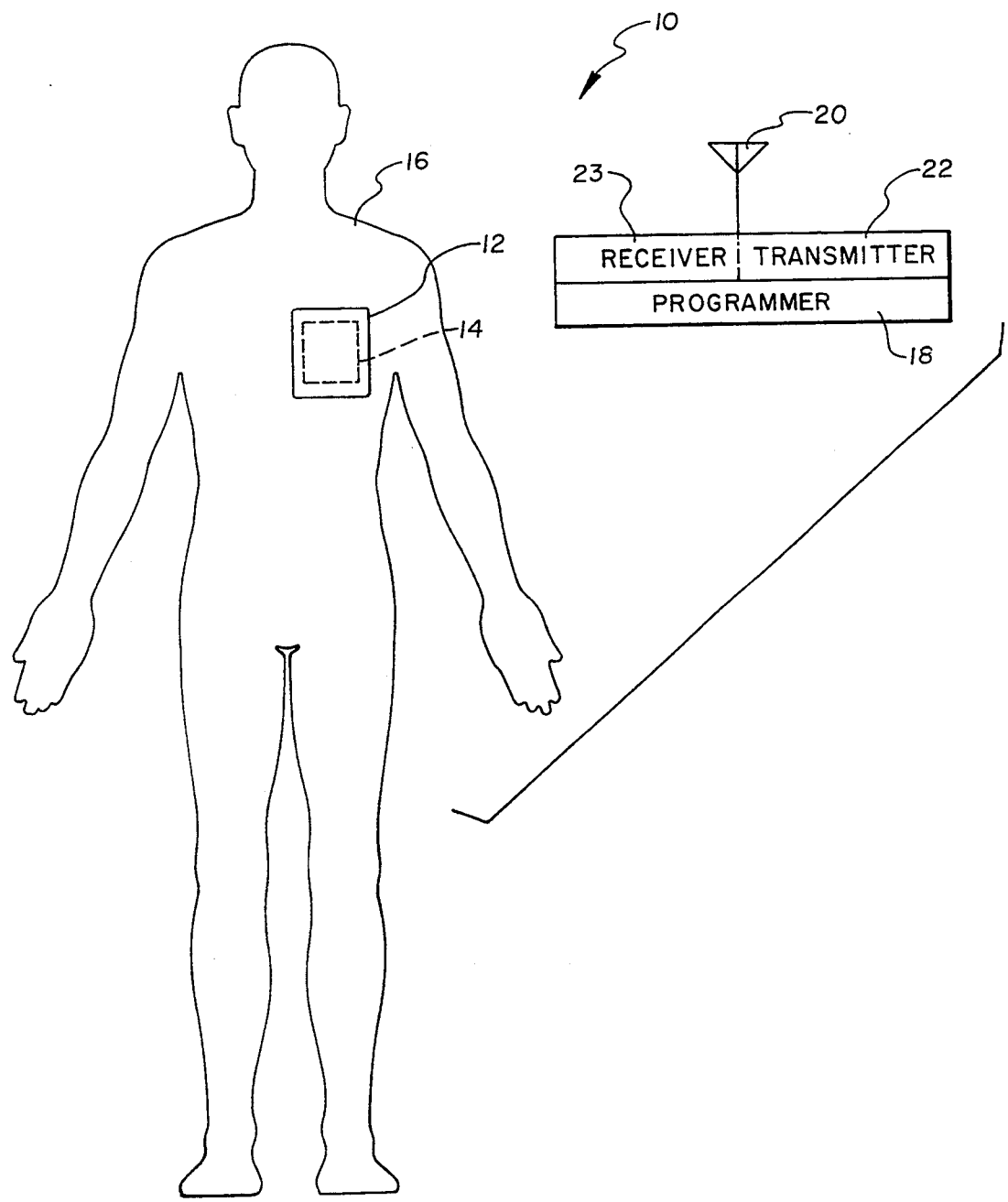
FIG. 1 illustrates a repeater system of the present invention in use.

FIG. 1 illustrates a repeater system 10 where a repeater 12, actually a transceiver, is placed over an implanted device 14 in a person 16. The implanted device 14 can be that such as, but not limited to a pacemaker or defibrillator. A programmer 18 sends programmed data for reception by the repeater 12 via an RF data link which is transmitted by an antenna 20. The received, programmed data information is transmitted from the repeater 12 to the implanted device 14. Information is also linked by telemetry via the component members to the programmer 18.

Figure 2:
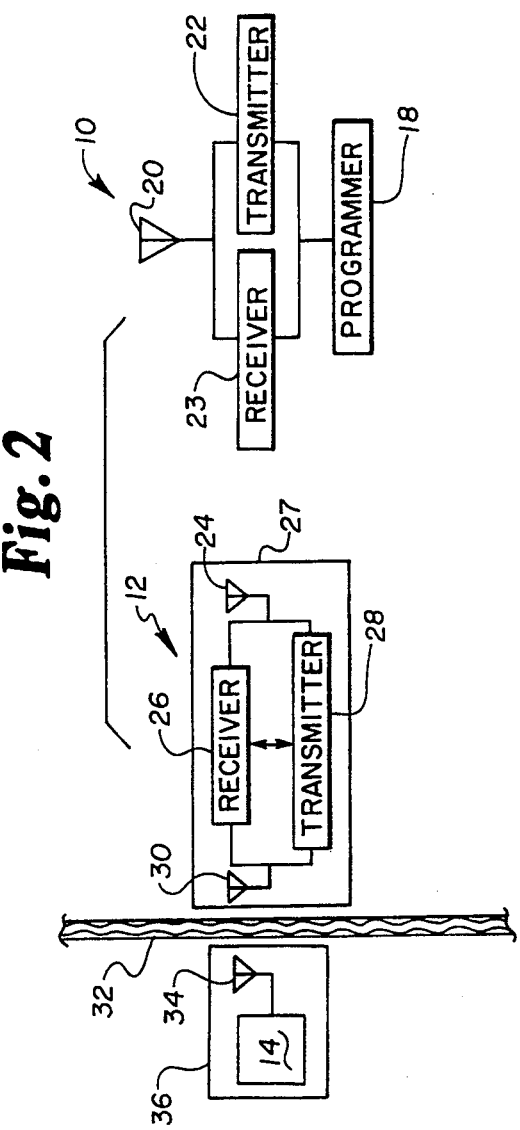
FIG. 2 illustrates a block diagram of the repeater system.

FIG. 2 illustrates a block diagram of the present invention where all numerals correspond to those elements previously described. Informational data derived in the programmer 18 is transmitted in the form of coded RF by a transmitter 22 and the antenna 20. A receiver 23 also connects to the antenna 20 and the programmer 18. This coded RF information is received by an antenna 24 and a receiver 26 integral to the repeater 12. The repeater 12 is contained in a plastic enclosure 27. This received information is rebroadcast by a transmitter 28 and antenna 30 integral to the repeater 12. The rebroadcast information travels through skin 32 of the patient, and is received by the antenna 34 which is connected to the implantable device 14. This received information then appropriately stimulates the implantable device 14. The implantable device 14 and the antenna 34 are encapsulated in an enclosure 36.

Conversely coded data information from the encapsulated implanted device 14 is sent via its integral antenna 34, through the skin 32, and to the antenna 30 of the repeater 12. The receiver 26 relays this coded information to the transmitter 28 and the antenna 24 where it is broadcast to the programmer unit 18 via antenna 20 and the receiver 23.

Figure 3:
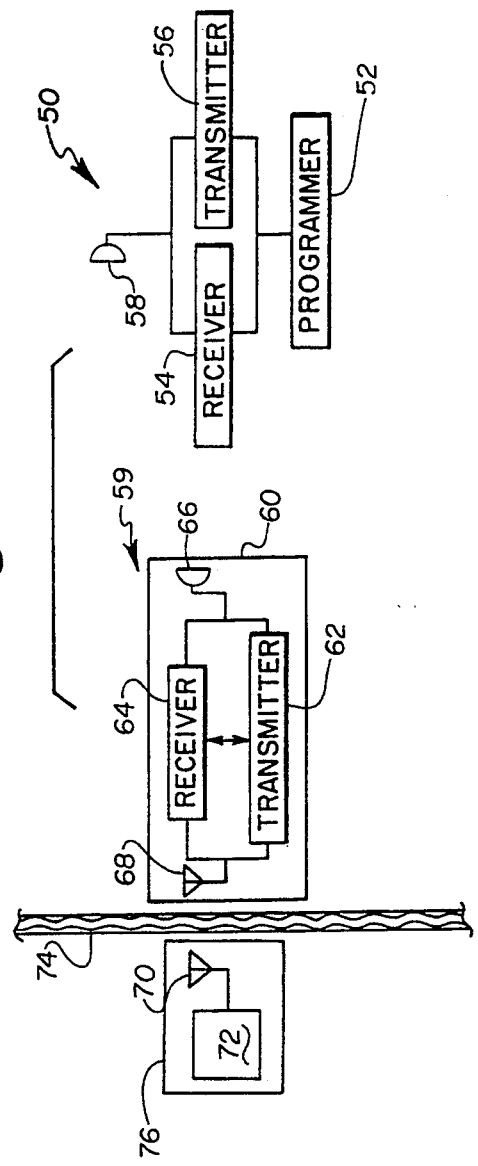
FIG. 3 illustrates an alternative embodiment of the repeater system.

FIG. 3, an alternative embodiment, illustrates a block diagram of the repeater system 50, similar to the repeater system 10 illustrated in FIG. 2 with the exception of the data link medium which may be an alternative transmission frequency or even a different medium, such as infrared or ultrasound. A programmer 52 electrically connects to the receiver 54 and transmitter 56. A suitable antenna 58 is utilized with the receiver 54 and the transmitter 56 depending on the data link medium.

The repeater 59 includes an enclosure 60, a transmitter 62, a receiver 64 and a medium suitable antenna 66 connected to the transmitter 62 and receiver 64. Another antenna 68 electrically connects the transmitter 62 and the receiver 64 to effect two-way communication between the antenna 70 which is integral to an implantable device 72 located beneath the skin layer 74. The antenna 70 and the implantable device 72 are encapsulated in an enclosure 76, which, of course, is implanted.

Various modifications can be made to the present invention without departing from the apparent scope hereof.

Other forms of communication can be utilized between the repeater and the programmer, such as infrared energy or ultrasonic which is within the teachings and scope of the present invention. Use of infrared energy between the repeater and the programmer would be considered as an alternative embodiment.

I claim:

1. A wireless programmer/repeater system for communicating with an implanted medical device in a patient comprising:

programmer means positioned remote from the patient for providing programming data to be communicated to the medical device; and repeater means physically separate from and not connected to the programmer means and positioned proximite to the patient for relaying the programming data from the programmer means to the medical device.

2. The wireless programmer/repeater system of claim 1 wherein the repeater means comprises:

first antenna means for communicating with the programmer means; and second antenna means for communicating with the medical device.

3. The wireless programmer/repeater system of claim 2 wherein the repeater means includes means for generating the program data in a first and a second code format and the first antenna means transmits and receives according to the first code format and the second antenna means transmits and receives according to the second code format.

4. The wireless programmer/repeater system of claim 1 wherein the repeater means is contained in a nonconductive enclosure.

5. The wireless programmer/repeater system of claim 1 wherein the repeater means is contained within an enclosure that is sterilizable and can be used in a sterile environment separate from and not physically connected to the programmer means.

6. The wireless programmer/repeater system of claim 1 further comprising radio frequency (RF) signal generation means for relaying the programming data between the programmer means and the repeater means in the form of radio frequency (RF) signals.

7. The wireless programmer/repeater system of claim 1 further comprising infrared signal generation means for relaying the programming data between the programmer means and the repeater means in the form of infrared signals.

8. The wireless programmer/repeater system of claim 1 further comprising ultrasonic signal generation means for relaying the programming data between the programmer means and the repeater means in the form of ultrasonic signals.

9. A wireless programmer/repeater system for communicating with an implanted medical device in a patient comprising:
   programmer means positioned remote from the patient for indirectly sending data to and receiving data from the medical device; and
   repeater means physically separate from and not connected to the programmer means and positioned proximite to the patient for relaying data between the programmer means and the medical device, 10. The wireless programmer/repeater system of claim 9 wherein the repeater means comprises:
    first antenna means for communicating with the programmer means; and
    second antenna means for communicating with the medical device.

11. The wireless programmer/repeater system of claim 10 wherein the repeater means includes means for generating the program data in a first and a second code format and the first antenna means transmits and receives according to the first code format and the second antenna means transmits and receives according to the second code format.

12. The wireless programmer/repeater system of claim 9 wherein the repeater means is contained in a nonconductive enclosure.

13. The wireless programmer/repeater system of claim 9 wherein the repeater means is contained within an enclosure that is sterilizable and can be used in a sterile environment separate from and not physically connected to the programmer means.

14. The wireless programmer/repeater system of claim 9 further comprising radio frequency (RF) signal generation means for relaying the programming data between the programmer means and the repeater means in the form of radio frequency (RF) signals.

15. The wireless programmer/repeater system of claim 9 further comprising infrared signal generation means for relaying the programming data between the programmer means and the repeater means in the form of infrared signals.

16. The wireless programmer/repeater system of claim 9 further comprising ultrasonic signal generation means for relaying the programming data between the programmer means and the repeater means in the form of ultrasonic signals.

* * * * *